US010151742B2

(12) United States Patent
Yaralioglu

(10) Patent No.: US 10,151,742 B2
(45) Date of Patent: Dec. 11, 2018

(54) DEVICE AND METHOD FOR MEASURING PHYSICAL PROPERTIES OF A MATERIAL

(71) Applicant: Goksen Goksenin Yaralioglu, Atasehir/Istanbul (TR)

(72) Inventor: Goksen Goksenin Yaralioglu, Atasehir/Istanbul (TR)

( * ) Notice: Subject to any disclaimer, the term of this patent is extended or adjusted under 35 U.S.C. 154(b) by 0 days.

(21) Appl. No.: 15/564,812

(22) PCT Filed: Apr. 6, 2015

(86) PCT No.: PCT/TR2015/000134
§ 371 (c)(1),
(2) Date: Oct. 6, 2017

(87) PCT Pub. No.: WO2016/163961
PCT Pub. Date: Oct. 13, 2016

(65) Prior Publication Data
US 2018/0113111 A1    Apr. 26, 2018

(51) Int. Cl.
| | | |
|---|---|---|
| *G01N 33/49* | (2006.01) | |
| *G01N 29/02* | (2006.01) | |
| *G01N 29/22* | (2006.01) | |
| *B01L 3/00* | (2006.01) | |
| *G01N 33/86* | (2006.01) | |

(52) U.S. Cl.
CPC .......... *G01N 33/4905* (2013.01); *B01L 3/508* (2013.01); *G01N 29/02* (2013.01); *G01N 29/222* (2013.01); *G01N 33/86* (2013.01); *G01N 2291/02466* (2013.01)

(58) Field of Classification Search
CPC .. G01N 33/4905; G01N 29/02; G01N 29/222; G01N 33/86; B01L 3/508
See application file for complete search history.

(56) References Cited

U.S. PATENT DOCUMENTS

| | | |
|---|---|---|
| 5,494,639 A | 2/1996 | Grzegorzewski |
| 6,402,704 B1 | 6/2002 | McMorrow |
| 6,418,968 B1 * | 7/2002 | Pezzuto ............ B01L 3/502738 137/833 |
| 6,537,501 B1 | 3/2003 | Holl et al. |
| 9,234,777 B2 * | 1/2016 | Ao .......................... G01F 1/662 |
| 2003/0029242 A1 | 2/2003 | Yaralioglu et al. |
| 2009/0114044 A1 | 5/2009 | Godfrey et al. |
| 2011/0207238 A1 | 8/2011 | Horii et al. |
| 2012/0294767 A1 | 11/2012 | Viola et al. |
| 2014/0187956 A1 * | 7/2014 | Rice ..................... B06B 1/0662 600/459 |
| 2014/0250985 A1 | 9/2014 | Shinobu et al. |

OTHER PUBLICATIONS

A. Voleisis et al.; "Ultrasonic method for the whole blood coagulation analysis"; Ultrasonics; 2002; pp. 101-107; vol. 40; Elsevier.

\* cited by examiner

*Primary Examiner* — David Z Huang
(74) *Attorney, Agent, or Firm* — Hayes Soloway PC

(57) ABSTRACT

A device is provided for measuring physical properties of a sample material having a body comprising a chamber adapted to receive a sample material and a transducer electrically connected to a circuit. The transducer is arranged on the body of the device to contact the body such that the body is able to transmit vibrations between the sample material and the transducer. A drive unit is electrically connectable to the circuit to measure physical properties of the sample material.

9 Claims, 5 Drawing Sheets

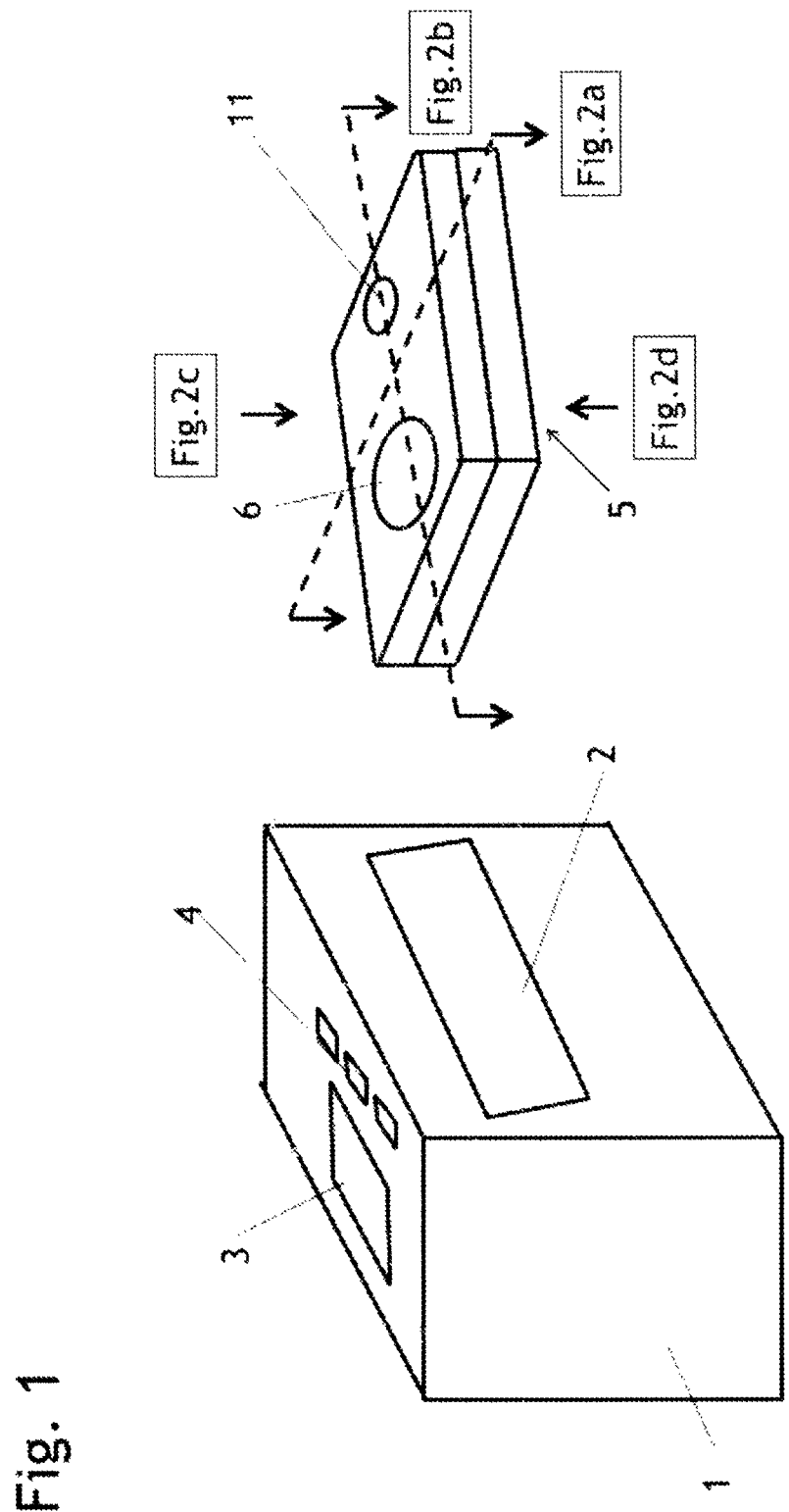

DEVICE AND METHOD FOR MEASURING PHYSICAL PROPERTIES OF A MATERIAL

TECHNICAL FIELD OF THE INVENTION

The present invention relates to a device and a method for measuring physical properties of a material and in particular to a device and a method for measuring coagulation time of blood and especially to a portable device for measuring coagulation time of blood employing an ultrasonic sensor and a method for measuring coagulation time of blood using ultrasound waves.

BACKGROUND OF THE INVENTION

Blood clotting occurs as a result of series of complex biological interactions. There are various factors, enzymes and proteins that affect the clotting process. Long coagulation times usually indicate lack of specific factors in the blood. Various tests such PT, aPTT have been developed to identify deficiency of these specific factors. Also, patients under regular drug therapy that changes blood viscosity should be monitored for blood coagulation time. Blood coagulation time measurement provides vital information regarding the patients.

For coagulation, various testing methods have been developed to detect the beginning of the coagulation process. Optical methods detect the changes in the optical properties of blood. Electrical methods depend on resistance or capacitance change. These methods are indirect since they measure a secondary effect due to blood coagulation. Direct methods on the other hand measure the viscosity changes of the blood during coagulation. So they are more dependable and immune to other factors such as high fat concentration that may affect the optical or electrical properties of blood. US2003/0029242 discloses a device for measuring the coagulation time of blood using an ultrasonic sensor. US2009/114044 discloses a docking mechanism for a biosensor apparatus.

Coagulation time measurements are usually done at hospitals or clinical labs. Patients are required to travel to these facilities. On the other hand, point-of-care testing removes the burden on the patients. It is fast and it prevents complications that may rise due to the late or no testing.

Therefore there is a need for a portable system that can measure the blood coagulation time using a direct measurement method.

DESCRIPTION OF THE INVENTION

It is an object of the present invention to provide a point-of-care system that can measure the coagulation time directly.

It is a further object of the present invention to provide a device which can be produced easily and cost effectively.

Current invention is defined by the appended claims, the content of which is included here by reference.

The present invention provides a device for measuring physical properties of a sample material having:
- a body comprising a chamber adapted to receive a sample material,
- a transducer electrically connected to a circuit, wherein the transducer is arranged to contact the body such that the body is able to transmit vibrations between the sample material and the transducer and wherein a drive unit is electrically connectable to the circuit to measure physical properties of the sample material. Accordingly, the body is able to transmit vibrations due to ultrasonic waves.

According to the invention, the transducer is arranged on the body to contact a surface of the body. The body comprises an inner surface defining the chamber and an outer surface and the transducer is arranged on the outer surface. The transducer is coupled to the outer surface of the body. The transducer may be glued, sputtered or deposited on the body. The transducer may be aligned to the chamber.

According to the invention, the body isolates the chamber and/or the sample material from the transducer; hence, the transducer does not contact the sample material.

The device according to the invention may further comprise a vibration transmitting member arranged between the transducer and the body for inducing and/or transmitting the vibrations in the chamber. The vibration transmitting member may be arranged to contact the body such that the body transmits vibrations between the sample material and the vibration transmitting member. The vibration transmitting member may be arranged to contact the transducer such that vibrations on the vibration transmitting member are transmitted to the transducer and vice versa. The vibration transmitting member may be a wave guide. The vibration transmitting member may be adapted to transmit ultrasonic waves.

The inner surface comprises a first wall part and a second wall part different than the first wall part, wherein the transducer and/or the vibration transmitting member is arranged closer to the second wall part than to the first wall part. The first wall part may be arranged on the opposite side of the second wall part; the first wall part may be preferably facing and/or parallel to the second wall part.

The body may comprise a first body layer and a second body layer attached to the first body layer. The chamber may be formed in the first body layer. The transducer may be arranged to contact the second body layer and/or the transducer may be arranged on the second body layer. The inner surface may be defined by the first body layer and the second body layer. The first body layer may comprise the first wall part. The second body layer may comprise the second wall part. The transducer and/or the vibration transmitting member may be arranged on a surface of the second body layer, which is on an opposite side to a side thereof comprising the second wall part. Preferably, the transducer or the vibration transmitting member may form the second body layer.

According to the invention, the transducer and/or the vibration transmitting member is arranged such that the transducer and/or the vibration transmitting member does not contact the sample material directly.

The chamber may be formed on a surface of the first body layer, which is covered by the second body layer.

Preferably, the chamber may be etched into the body, preferably into the first body layer. The chamber is covered by the second body layer.

Preferably, the chamber may comprise a square shaped cross section. The first wall part and the second wall part may be at opposite sides of the square shaped cross section.

The device according to the invention may further comprise a drive unit in contact with the electrical circuit. The drive unit may comprise a detector. The detector is arranged such that electrical resistance, voltage, current or waveform changes in the transducer are detectable by the detector. The drive unit may further comprise an actuator adapted to induce vibrations on the transducer.

The device according to the invention may further comprise a housing comprising the drive unit and adapted to be coupled with the body. The transducer may be arranged on the housing such that when the housing is coupled with the body, the transducer is able to contact the body and/or the vibration transmitting member such that the body is able to transmit vibrations between the sample material and the transducer. The vibration transmitting member may be arranged on the housing and/or on the body.

Alternatively, the housing may comprise a first electrical contact. The body may comprise a second electrical contact and the first electrical contact and the second electrical contact are able to contact each other, when the housing is coupled with the body.

According to the invention, the transducer may be a piezoelectric transducer or piezoelectric sensor, preferably made of ZnO or PZT. The body may be made of a solid material, glass, quartz or silicon.

According to the invention, the vibration frequency applied by the transducer may be between 100 MHz-1 GHz and preferable about 400 MHz. The drive unit may be adapted to induce vibrations on the transducer having a frequency of 100 MHz-1 GHz and preferable of about 400 MHz.

The body is formed as disposable cartridge.

The first body layer may comprise a first opening connected to the chamber for introducing the sample material into the chamber and a second opening connected to the chamber for evacuating the chamber.

The sample material may be a fluidic material, preferably being blood. The chamber may have a microfluidic channel where the blood is loaded. The channel may be aligned with the transducer.

The transducer according to the invention may be a high frequency transducer.

The present invention provides a method for measuring physical properties of a sample material comprising:
  providing a sample material in a chamber formed in a body of a device for measuring physical properties of a sample material, wherein the chamber is defined at least by a first body wall part and a second body wall part;
  providing a transducer arranged to contact the body at a side closer to the second body wall part than to the first body wall part;
  applying vibrations to the body using the transducer;
  detecting the vibrations using the transducer, which have been reflected by first body wall part; and
  measuring physical properties of the sample material depending on the vibrations reflected by first body wall part.

According to the inventive method, the transducer generates high frequency sound waves and these sound waves reflect from the channel after propagating in the blood. The reflected waves are again collected by the transducer and they are converted into electrical signals. The reader unit makes electrical contacts to the transducer and it applies electrical pulses and collects the reflected waves. When the blood coagulation starts, the attenuation in the blood increases and by measuring the reflected wave amplitude one can monitor the coagulation process.

Current invention provides also a cartridge adapted to be coupled to a device for measuring physical properties of a sample material, the cartridge having a body comprising a first body layer and a second body layer connected to the first body layer, wherein the first body layer comprises a chamber, which is adapted to receive a sample material, and wherein the second body layer is able to transmit vibrations between the sample material and a transducer contacting the second body layer.

Current invention provides a device for measuring physical properties of a sample material comprising a transducer, a drive unit electrically connected to the transducer to measure physical properties of the sample material, and a housing adapted to be coupled to a cartridge comprising the sample material, wherein the transducer contacts the cartridge and the cartridge is adapted to transmit vibrations between the sample material and the transducer.

In order to ease the production, current invention provides a disposable cartridge having a multi-layered structure for using in a measuring device having a drive unit to emit and receive ultrasonic waves to and from the disposable cartridge for measuring physical properties of blood, the disposable cartridge comprising a first layer defining a chamber for storing a blood sample and a second layer attached to the first layer for transmitting ultrasonic waves to and from the blood sample stored within the chamber. Namely, the second layer transmits ultrasonic waves between the blood sample and the drive unit, when the cartridge is coupled with the measuring device.

The first layer and the second layer are attached to each other planarly and/or such that the second layer covers the chamber formed in the first layer.

A transducer and an electrical circuit connected to the transducer may be arranged on the second layer on a surface in opposite direction to the first layer. Accordingly, the electrical circuit is electrically connectable to the drive unit driving the transducer, when the cartridge is coupled with the measuring device.

The transducer is able to convert electrical signals from the drive unit to ultrasonic waves and vice versa.

An adhesive layer may be arranged between the first layer and the second layer for attaching them to each other. Alternatively, the first layer and the second layer are attached by using bonding technique.

A further adhesive layer may be arranged between the second layer and the transducer and/or the electrical circuit for attaching the transducer and/or the electrical circuit to the second layer.

The first layer may include one or more holes connecting to the chamber through one or more channels.

Accordingly, the current invention provides a method for production of a disposable cartridge for using in a measuring device having a drive unit to emit and receive ultrasonic waves to and from the disposable cartridge for measuring physical properties of blood, comprising:
  providing a first layer;
  forming a chamber in the first layer;
  providing a second layer; and
  attaching the first layer with the second layer to form a body of the disposable cartridge.

The first layer and/or the second layer may be made of glass, quartz or silicon. The first layer and/or the second layer may be made of different materials.

Forming the chamber may comprise etching the chamber in the first layer.

Attaching the first layer with the second layer may comprise providing an adhesive layer between the first layer and the second layer.

The first layer and the second layer are attached to each other planarly and/or such that the second layer covers the chamber formed in the first layer.

The method further comprises providing a transducer and an electrical circuit on the second layer on a surface opposite to the first layer, wherein a first electrode of the circuit is provided onto the second layer, the transducer is provided onto the first electrode and then a second electrode of the circuit is provided onto the transducer.

The method may further comprise providing a further adhesive layer between the second layer and the transducer and/or the electrical circuit for attaching the transducer and/or the electrical circuit to the second layer.

The method may further comprise drilling one or more holes into the first layer which connect to the chamber through one or more channels.

These and further advantages of the current invention are disclosed in the appended claims.

DESCRIPTION OF THE DRAWINGS

The above disclosed and further features of the current invention will be better understood with the following detailed description and drawings of the preferred embodiments of the invention.

FIG. 1 is a schematic representation of a device for blood coagulation time measurement.

DESCRIPTION OF PREFERRED EMBODIMENTS

Figure 2A:
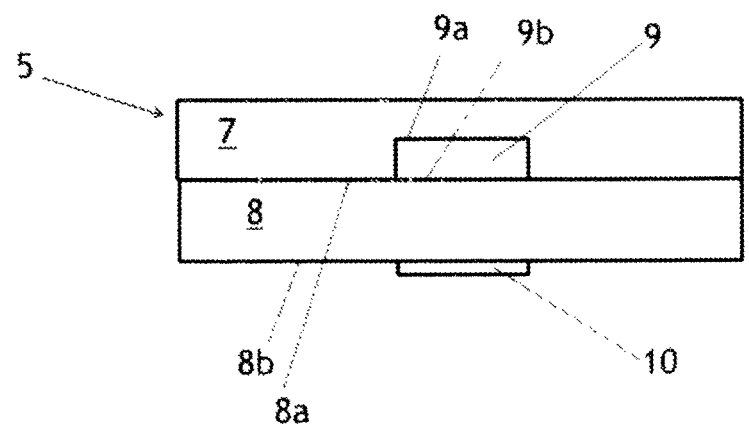
FIG. 2a, 2b, 2c, 2d show respectively cross-sectional views of a first side and a neighboring second side and a top view and a bottom view of a preferred embodiment of a device according to the invention.

Preferred embodiments of the current invention will be described with references to the appended drawings.

FIG. 1 shows a representation of the device for the coagulation time measurement system according to the invention. Accordingly, the device comprises a body 5. A housing 1 contains the electronics forming a drive unit that drive a transducer 10 arranged on the body 5. Alternatively, the transducer 10 may be arranged at the housing 1. In this exemplary embodiment, the body 5 is formed as a cartridge. The housing 1 has an opening 2 where the body 5 of the cartridge is inserted. Inside the housing 1, there is a mechanism to make electrical contacts to the body 5. The housing 1 has a display unit 3 to display the measurement results. It has also a set of keys 4 to control the functions of the reader. The cartridge 5 has a hole 6 to load the blood in. Preferably, a user can prick a finger and form a blood droplet on his/her finger and put the blood sample into this hole 6. The body has a small hole 11 to provide a route for air to escape from the microfluidic channel forming a chamber 9 for receiving the blood sample.

FIG. 2a shows a cross-sectional view of a device according to an embodiment of the invention. Accordingly, the device comprises a body 5 in form of a cartridge. The cartridge body 5 can be made of two pieces, a first layer 7 forming a top piece and a second layer 8 forming a bottom piece attached to the first layer 7. The microfluidic channel forming the chamber 9 is etched into the top piece where the holes are also drilled. Alternatively, the microfluidic channel forming the chamber 9 may be formed in other ways known to the person skilled in the art. The second layer 8 forming the bottom piece has the transducer 10 on its bottom surface 8b opposite to the first layer 7. The transducer 10 is made of a piezoelectric material and it may be glued, sputtered or deposited onto the bottom piece. Both pieces can be made preferably from glass, quartz or silicon. To form the cartridge body 5, top 7 and bottom 8 pieces may be glued together using a glue layer or using a bonding technique. The transducer 10 is aligned to the chamber 9 as shown in the figure. The microfluidic channel forming the chamber 9 runs from the big hole 6 to the small hole 11. The cross section of the microfluidic channel is preferably square. A top surface 8a of the second layer 8 covers the chamber 9 hence forming a bottom wall 9b of the chamber 9.

Figure 2B:
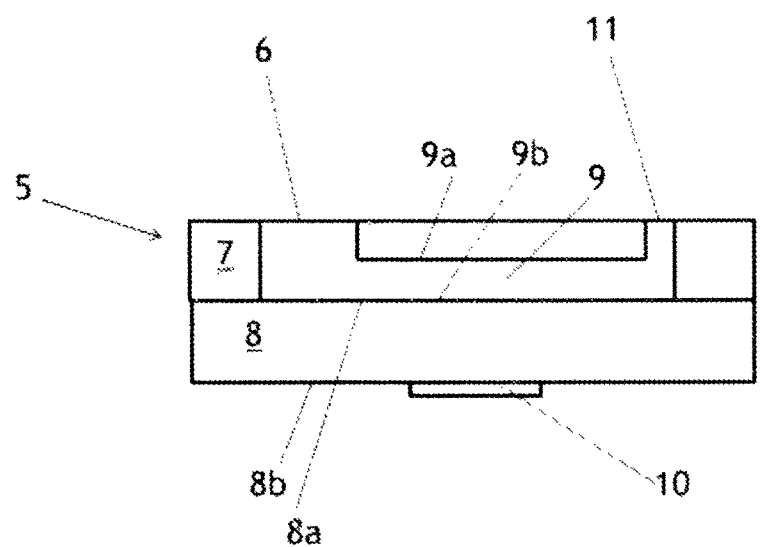

FIG. 2b shows a cross-sectional view of the cartridge body 5 along a longitudinal direction thereof. When blood is put through the big hole 6, it is get sucked into the channel due to the capillary forces. The small hole 11 provides an escape route for the air while blood is filling the channel.

Figure 2C:
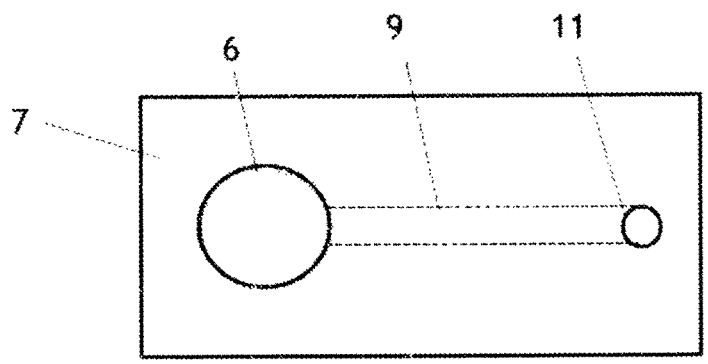

FIG. 2c shows a top view of the cartridge body 5.

Figure 2D:
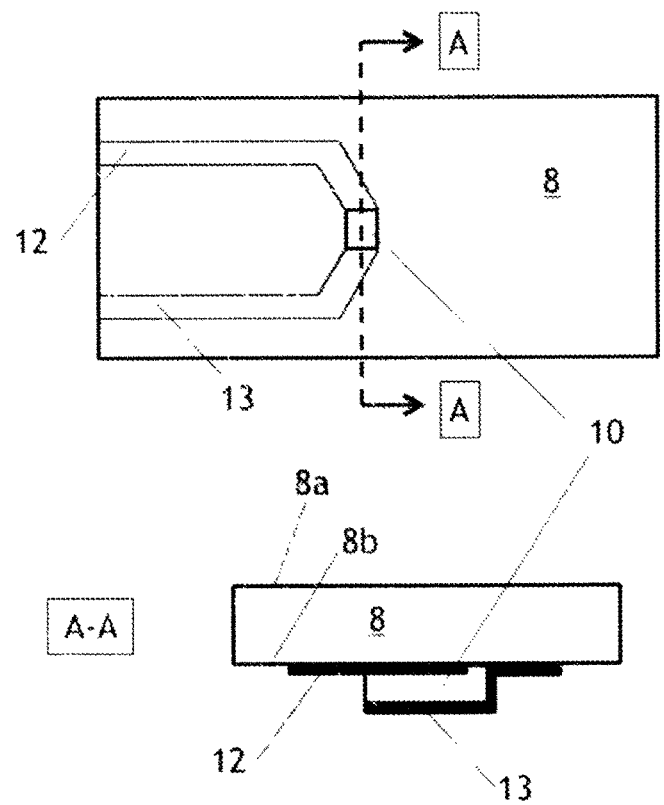

FIG. 2d shows the bottom view of the cartridge body 5 and a cross-section of the cartridge body 5 showing the arrangement of the transducer 10 on the cartridge body 5. There are two electrodes 12, 13 to provide contact to the transducer 10. The electrodes 12, 13 run on the cartridge body surface from the transducer 10 to the edge of the cartridge body 5. At the edge of the cartridge body 5, the housing 1 makes contact to these electrodes 12, 13. The electrodes 12, 13 can be made of gold, aluminum or any other material that is conducting electricity. The transducer 10 is sandwiched between top 13 and bottom 12 electrodes. When an electrical signal is applied to the electrodes 12, 13, the transducer 10 vibrates and it emits sound waves into the bottom piece. The vibration frequency is preferable around 400 MHz. The sound waves propagate along the thickness of the bottom piece. When they reach to the bottom wall 9b of the chamber 9, some portion of the waves reflect back and some portion is transmitted into blood. After propagating in the blood the transmitted waves reflect back from the top wall 9a of the chamber 9 which is on an opposite side of the bottom wall 9b. These reflections are collected back by the transducer 10 and they are converted into electrical signals.

Figure 3:
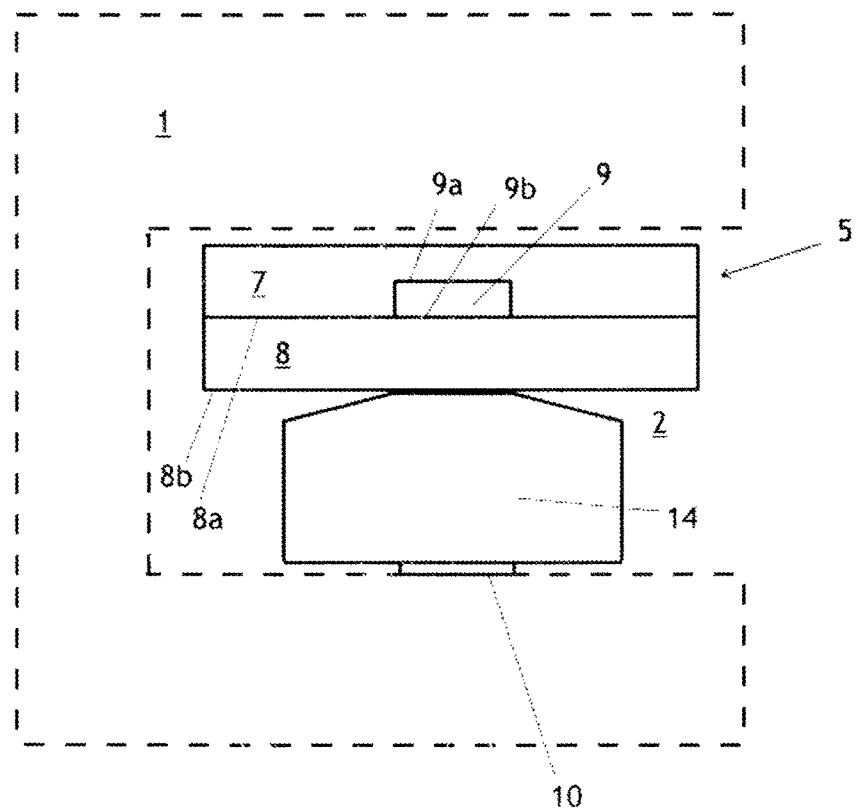
FIG. 3 is a schematic side view of a further preferred embodiment of the device according to the invention.

FIG. 3 shows a device according to a further embodiment of the invention. In this alternative embodiment, the transducer 10 is not integrated with the cartridge body 5 but it is arranged in the housing 1 adapted to be remotely contact the bottom surface of the cartridge body 5 through a vibration transmitting member 14. FIG. 3 shows a cross-section of the housing 1. The vibration transmitting member 14 and the transducer 10 are placed in the housing 1. Alternatively, the vibration transmitting member 14 may be arranged on the bottom surface of the cartridge body 5. In this embodiment, there are no electrical connections between the housing 1 and the cartridge body 5. This configuration reduces production costs of the cartridge.

Figure 4:
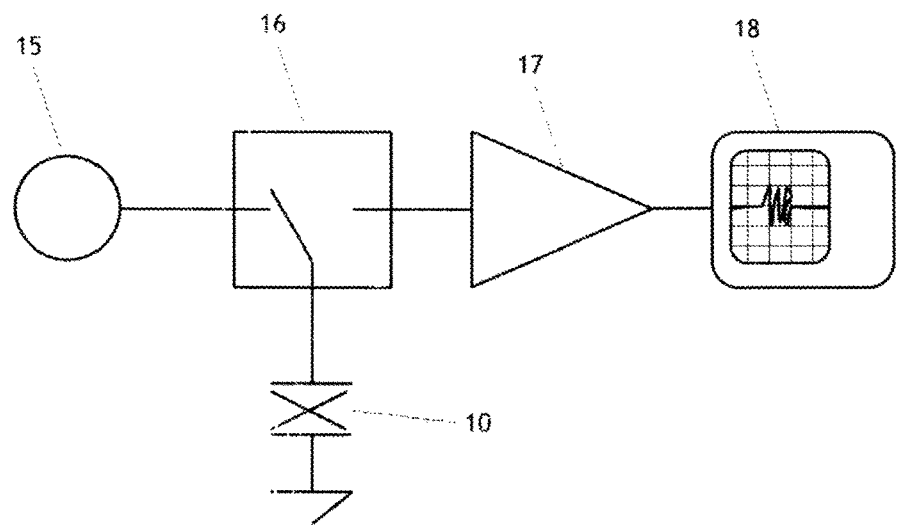
FIG. 4 is a schematic representation of a drive unit for the transducer.

FIG. 4 shows the signal emission/reception electronics forming the drive unit. A signal generator 15 generates burst of sinusoidal signals. These signals are applied to the transducer 10 via a DPST (double pole single throw) switch 16. In the emission cycle, the switch 16 connects the signal generator 15 to the transducer 10. The applied electrical signal is converted into high frequency ultrasound at the transducer 10 and the transducer 10 generates sound waves in the cartridge body 5. During reception cycle, the switch 16 connects the transducer 10 to a reception amplifier 17. During reception, reflections from the chamber 9 are collected by the transducer 10 and they are converted into electrical signals. The amplifier 17 amplifies the reflections and these reflections can be observed on an oscilloscope screen 18.

Figure 5:
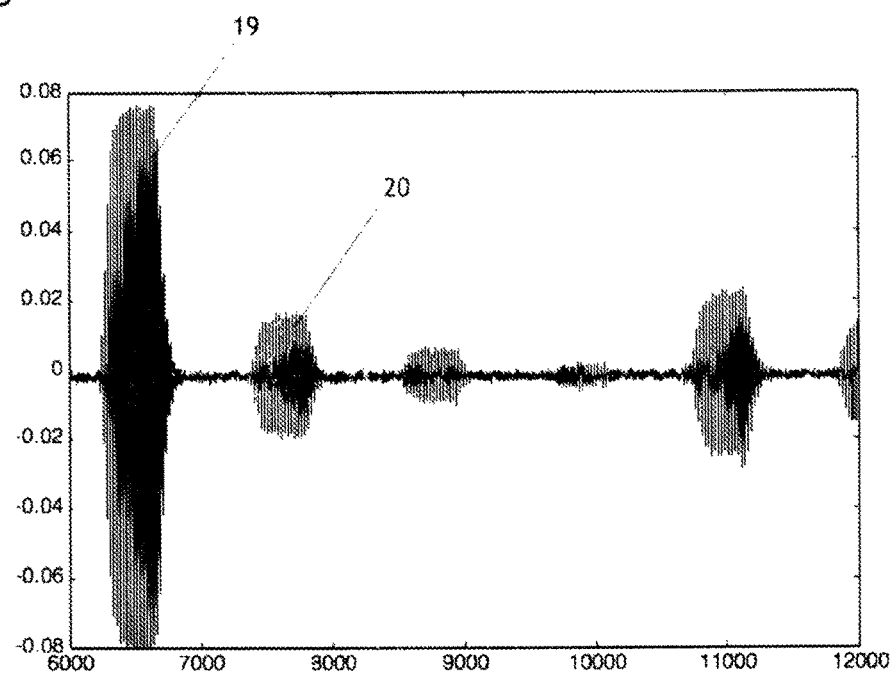
FIG. 5 is a schematic graph of ultrasonic reflections from a chamber in a device according to the invention.

FIG. 5 shows a typical reflection wave form obtained using the circuit shown in FIG. 4. A pulse 19 is the first reflection from the bottom wall 9b of the chamber 9 after propagating through the half thickness of the body 5, namely through the second layer 8. A second reflection 20 comes from the top wall 9a of the chamber 9 after propagating through the blood and half thickness of the body 5 (thickness of the second layer 8). The amplitude of the reflection 20 is affected by the blood viscosity. As the viscosity increases, the amplitude decreases.

Figure 6:
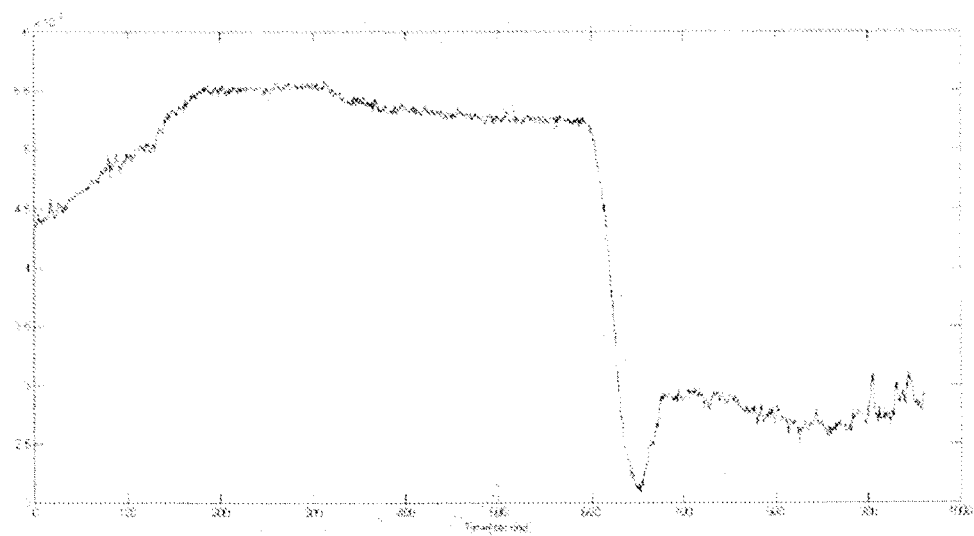
FIG. 6 is a schematic graph of blood reflection amplitude as a function of time.

FIG. 6 shows the amplitude of the reflected wave from the top surface of the chamber 9. At the beginning there are small fluctuations when the blood is filling the chamber 9. After 600 seconds, the amplitude reduces quickly. This is when the coagulation takes place. By measuring the amplitude change, the coagulation time is determined.

The preferred embodiment of the invention is described above in the Drawings and Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings.

The embodiment was chosen and described in order to best explain the principles of the invention and its practical application and to enable others skilled in the art to best utilize the invention in various embodiments and with various modifications as are suited to the particular use contemplated.

The invention claimed is:

1. A disposable cartridge adapted to connect to a drive unit of a measuring device having a housing for measuring physical properties of a sample material, the disposable cartridge having a body comprising a first body layer and a second body layer attached to the first body layer, wherein the first body layer comprises a chamber to receive a sample material, wherein the second body layer is able to transmit vibrations between the sample material and a transducer contacting the second body layer,
wherein the transducer and an electrical circuit connected to the transducer are arranged on the second body layer on a surface in opposite direction to the first body layer, wherein the drive unit is electrically connectable to the electrical circuit, when the housing is coupled with the body,
characterized in that a first electrode of the circuit is provided on the second layer, the transducer is provided on the first electrode and a second electrode of the circuit is provided on the transducer to provide contact to the transducer.

2. The cartridge according to claim 1, wherein the chamber is formed on a surface of the first body layer, which is covered by the second body layer.

3. The cartridge according to claim 1, wherein the transducer is attached to or formed on a surface of the second body layer.

4. The cartridge according to claim 1, wherein the first body layer comprises a first opening connected to the chamber for introducing the sample material into the chamber and a second opening connected to the chamber for evacuating the chamber.

5. A method for production of a disposable cartridge adapted to connect to a drive unit of a measuring device having a housing to emit and receive ultrasonic waves to and from the disposable cartridge for measuring physical properties of a sample material, comprising:
providing a first layer;
forming a chamber in the first layer to receive the sample material;
providing a second layer;
characterised by providing a transducer and an electrical circuit on the second layer on a surface in opposite direction to the first layer, wherein a first electrode of the circuit is provided onto the second layer, the transducer is provided onto the first electrode and a second electrode of the circuit is provided onto the transducer to provide contact to the transducer; and
attaching the first layer with the second layer to form a body of the disposable cartridge such that the second body layer is able to transmit vibrations between the sample material and the transducer.

6. The method according to claim 5, wherein forming the chamber comprises etching the chamber in the first layer.

7. The method according to claim 5, wherein attaching the first layer with the second layer comprises providing an adhesive layer between the first layer and the second layer.

8. The method according to claim 7, further comprising providing a further adhesive layer between the second layer and the transducer and/or the electrical circuit for attaching the transducer and/or the electrical circuit to the second layer.

9. The method according to claim 5, further comprising drilling one or more holes into the first layer which connect to the chamber through one or more channels.

* * * * *